United States Patent [19]

Davies

[11] Patent Number: 5,849,569
[45] Date of Patent: Dec. 15, 1998

[54] ASSESSMENT OF BONE CELL ACTIVITY

[75] Inventor: John E. Davies, Toronto, Canada

[73] Assignee: Millenium Biologix, Inc., Ontario, Canada

[21] Appl. No.: 448,427

[22] PCT Filed: May 18, 1994

[86] PCT No.: PCT/CA94/00285

§ 371 Date: Jul. 12, 1995

§ 102(e) Date: Jul. 12, 1995

[87] PCT Pub. No.: WO94/26872

PCT Pub. Date: Nov. 24, 1994

[30] Foreign Application Priority Data

May 18, 1993 [GB] United Kingdom ............... 9310194

[51] Int. Cl.$^6$ ..................................................... C12M 3/04
[52] U.S. Cl. ................................. 435/288.3; 435/288.4; 435/305.1; 435/305.2; 435/305.4; 427/2.11; 427/2.27; 359/396; 359/398
[58] Field of Search .................. 435/287.9, 288.1–288.4, 435/288.7, 289.1, 292.1, 299.1, 304.1–305.4; 427/2.11, 2.27, 376.1; 423/309, 311; 359/396, 398; 428/426, 688, 332, 334

[56] References Cited

U.S. PATENT DOCUMENTS

| 4,655,777 | 4/1987 | Dunn et al. ............................ 623/16 |
| 4,770,943 | 9/1988 | Hakamatsuka et al. ............... 428/471 |
| 4,861,733 | 8/1989 | White .................................... 501/1 |
| 4,951,097 | 8/1990 | Oguchi . | |
| 5,018,847 | 5/1991 | Ojima et al. .......................... 350/534 |
| 5,128,169 | 7/1992 | Saita et al. ............................ 427/2.27 |
| 5,141,576 | 8/1992 | Shimamune et al. ................. 427/2.27 |

FOREIGN PATENT DOCUMENTS 0 532 421 3/1993 European Pat. Off. .
1 522 182 8/1978 United Kingdom .

OTHER PUBLICATIONS

Cells Mater. (1993), 3(3), "Osteoclastic Resorption Of Calcium Phosphate Ceramic Thin Films"; by J.E. Davies et al; pp. 245–256.

J. Biomed, Mater. Res. (1993), 27(4), "Histological and biochemical evaluation of osteoblasts cultured on bioactive glass, hydroxylapatite, titanium alloy, and stainless steel"; by W.C.A. Vrouwenvelder, et al; pp. 465–475.

Journal Of Bone And Mineral Research, vol. 7, No. 3, Mar. 1992, "An Assay System Utilizing Devitalized Bone for Assessment of Differentiation of Osteoclast Progenitors"; by Shigeru Amano, et al; pp. 321–328.

Bone And Mineral, vol. 6, No. 3, 1989, "The effect of substrate composition and condition on resorption by isolated osteoclasts"; by H. Shimizu, et al; pp. 261–275.

Journal Of Cell Science, vol. 66, No. 3, Mar. 1984, "Resorption Of Bone By Isolated Rabbit Osteoclasts"; by T.J. Chambers, et al; pp. 383–399.

Database WPI, Section Ch, Week 9321, Derwent Publications Ltd., London, GB; Class D22, AN 93–171861 and JP,A,5 103 829 (Shingijutsu Jigyodan) 27 Apr. 1993.

Primary Examiner—William H. Beisner
Attorney, Agent, or Firm—Bell Seltzer Intellectual Property Law Group of Altston & Bird LLP

[57] ABSTRACT

A calcium phosphate based thin film on which bone cells may be cultured to permit evaluation of bone cell functional properties comprises calcium phosphate entities which provide for varying degrees of resorption of the calcium phosphate entities in evaluating the functional properties. The film is sufficiently thin that resorption of the entities can be detected. Such film, as applied to a support, is a very useful analytical component for evaluating such bone cell functional characteristics. An analytical device, which may be used in an analytical kit, can be provided having a plurality of wells with the devices located at the bottom thereof. A process is provided for making the film and especially the film which has a combination of calcium hydroxyapatite with tricalcium phosphate.

15 Claims, No Drawings

ASSESSMENT OF BONE CELL ACTIVITY

FIELD OF THE INVENTION

This invention relates to the assessment of bone cell activity, such as osteoclast activity, which is useful in the analysis of normal bone cell processes, the determination of various metabolic bone diseases, such as osteoporosis in humans, and the evaluation of potential drug treatments to influence bone cell activity.

BACKGROUND OF THE INVENTION

There are two types of bone cells, those which make bone, osteoblasts, and those which resorb bone, osteoclasts. These cells have very precise functions and the balance between their activities is critical to the maintenance of the skeletal system. For example, in human adults, between 10 to 15% of trabecular bone surfaces are covered with osteoid (new unmineralized bone made by osteoblasts) while about 4% have active resorptive surfaces. The dynamic nature of the continuing flux of bone cell activity is illustrated by the calculation that approximately 18% of total skeletal calcium may normally be removed and deposited over a period of one year.

Osteoclasts, which resorb bone are not only of central importance in modelling abnormalities such as osteoporosis which is characterized by hypofunction, and Paget's disease where increased bone resorptive activity is seen, but also in some of the major so called metabolic bone diseases. The term metabolic bone disease refers to skeletal disorders which are generalized throughout the skeleton and thus there are no normal areas of bone in the skeleton. In these disease processes, the normal function of bone cells is modified. To assess the degree of perturbation of cell behaviour and how this may be further modified by the action of pharmaceutical agents is of central importance to both an understanding of the disease processes and the functions of the cells themselves.

The activity of osteoclasts in vivo can only be measured with animal models, where the sequelae of the activities of these cells are assessed by histological means or biochemical measurements e.g. of serum calcium levels. Several research groups have developed methods to directly observe the activity of isolated osteoclasts in vitro. Considerable success has been achieved when osteoclasts, isolated from bone marrow cell populations have been cultured on thin slices of either sperm whale dentine (Boyde et al Brit. Dent. J. 156, 216, 1984) or bone (Chambers et al J. Cell Sci. 66, 383, 1984). The latter group have been able to show that this resorptive activity is not possessed by other cells of the mononuclear phagocyte series (Chambers & Horton, Calcif Tissue Int. 36, 556, 1984). More recently, attempts to use other cell culture techniques, to study osteoclast lineage have still had to rely on the use of cortical bone slices (Amano et al. and Kerby et al J. Bone & Min. Res. 7(3), pp. 321–328 and 353–362, respectively) and it is increasingly obvious that quantitation of the resorption activity relies upon either two dimensional analysis of resorption pits of variable depth or stereo mapping of the resorption volume. Such techniques can usually provide an accuracy in result of about 40 to 60%. The latter provides far greater accuracy perhaps up to 70%, when assessing resorption of relatively thick substrata but is very time consuming and requires highly specialized equipment and training, and thus does not provide a potentially easy approach to this problem.

Furthermore, the preparation and subsequent examination of bone or dentine slices is neither an easy nor practical solution for the assessment of osteoclast activity. Specifically, these substrata cannot be proposed for routine use outside the highly specialized research laboratory environment. However, the use of artificial calcium phosphate preparations as substrata for osteoclast culture, has met with little success. Jones et al (Anat. Embryol 170, 247, 1984) reported that osteoclasts will resorb synthetic apatites in vitro but failed to provide experimental evidence and more recently Shimizu et al (Bone and Mineral 6, 261, 1989) have reported that isolated osteoclasts will resorb only devitalized bone surfaces and not synthetic calcium hydroxyapatite. These results would indicate that artificial surfaces are not worth pursuing.

Another technique in evaluating metabolic bone diseases is determining the amount of calcium in body fluid. Japanese Patent 04184256 published Jul. 1, 1992 discloses the use of a polyacrylamide gel in evaluating the extent of calcium in body fluid. Calcium is deposited on the gel and then the extent of deposited calcium is measured optically. The calcium is deposited by the use of a component that induces calcification. Preferably the body fluid is blood which is then treated to cause calcification and deposited calcium on the gel for subsequent optical measurement. The problem with this type of assay is that the source of the calcium cannot be determined.

Other techniques involving the use of light transmission are disclosed in U.S. Pat. No. 4,951,097. Two different monochromatic photographs of the bone specimen are used to calculate the calcified bone, osteo and bone marrow regions. Extraction however of a piece of bone involves surgery which can lead to a different set of complications.

Considerable work has also been done with respect to weightlessness or patients being confined to beds for long periods. Russian Patent 1,139,414 published Feb. 15, 1985 discloses the evaluation of the speed of physiological reconstruction of bone tissue. This value is calculated from a total loss of calcium from the patient over the period under investigation, the speed of physiological reconstruction of the bone under investigation and a total mass of renewed calcium. This technique is of particular interest in monitoring the condition of astronauts.

While most people are aware of how muscles will waste away without use, so bone mass will be lost in similar circumstances. Loss of bone mass is critical in many disease processes, (e.g. osteoporosis) but is also of considerable importance following injury, confinement to bed and even more recently, during extended space flight when normal gravitational forces cannot stimulate bone activity. Osteoblasts and osteoclasts, however, do not act independently of each other and much circumstantial evidence exists for cell signalling between these two cells (Heersche, J. N. M., Calcif. Tiss. Res. 26, 81–84 (1978)) although little is understood of these complex processes. The actions and interactions of bone cells is therefore of interest to diverse groups of researchers from those responsible for designing exercise regimes for astronauts to physicians treating metabolic bone diseases. Manufacturers producing, and surgeons implanting prostheses in bones are also equally interested in understanding how the materials they use can upset (or improve) the delicate balance of bone cell activity. For these reasons, the pharmaceutical industry is also involved with this area of research and, in particular, in finding out how drugs may influence the activity of, and balance between, these cells.

SUMMARY OF THE INVENTION

We have developed, in accordance with this invention, synthetic calcium phosphate films as culture substrata for bone cells and in particular, osteoclasts. The purpose of a thin film is to provide a more convenient means, than was hitherto unavailable, of assessing the resorptive activity of osteoclasts.

The film of this invention can be fabricated in a reproducible manner suitable for use as an analytical test to assay the resorptive activity of either human or animal osteoclasts as a result of disease or treatment with pharmaceutical or other bioactive agents, or mechanical, chemical or physical environmental changes. Specifically, the wholly artificial substrata or film may be inexpensively packaged in the form of an analytical kit for assessing osteoclast activity.

The system of the invention may be used in clinical drug screening programs. By use of the film of this invention, a variety of analytical techniques may be employed to establish front runner compounds for the treatment of metabolic bone diseases, such as osteoporosis based on their effect on osteoclast activity.

The invention as it resides in the assessment of bone cell activity may also be used as an analytical kit in determining a patient's bone cell activity, such as osteoclast activity, and hence susceptibility or degree of metabolic bone disorder. The system is also useful in studying the effect of reduced gravitational forces on osteoclasts. The analytical kit may be employed in space to determine osteoclast activity while under reduced gravitational forces.

According to another aspect of the invention, a process is provided to make the film by a sol-gel coating technique. An additional aspect is the provision of a process for culturing osteoclast cells on-the new film.

According to another aspect of the invention, a calcium phosphate based thin film on which bone cells may be cultured to permit evaluation of bone cell functional properties is provided:

the thin film comprising calcium phosphate entities which provide for varying degrees of resorption of the calcium phosphate entities in evaluating the functional properties, the film being sufficiently thin that resorption of said entities can be detected by a physical disappearance of calcium phosphate entities.

According to a further aspect of the invention, a component for use in an analytical or diagnostic test for evaluating bone cell functional characteristics, the component comprises:

a film substrate for supporting a film applied thereto;

a calcium phosphate based film on which bone cells may be cultured, the film having the above composition.

According to a further aspect of the invention, an analytical or diagnostic device for use in a system for evaluating bone cell characteristics, the device comprises:

a containment well;

a substrate provided on the bottom of the well;

the substrate having a film of the above composition applied thereto;

the substrate being positioned in the well with the film positioned upwardly of the well;

means for dividing the film surface into discreet test zones, if the film substrate is larger than a single test zone; and means for covering the well until used.

In accordance with a further aspect of the invention, a process for making a film having the above properties, the sol-gel process comprises:

combining a solution of an ammonium phosphate with a solution of a calcium nitrate over an extended period to form a sol-gel;

applying a film of the sol-gel on at least one surface of the substrate, and sintering the film coated substrate to form a solid film of calcium hydroxyapatite and/or tricalcium phosphate;

the relative amount and morphology of the calcium hydroxyapatite and tricalcium phosphate thin film being determined by varying conditions in the step of preparing the sol and sintering the film, the variable conditions being one or more of parameters in making and preparing the sol which include degree and extent of mixing during and after preparation of the sols, the duration of aging following sol peparation and sintering parameters which include temperature and sintering in a selected atmosphere.

In accordance with another aspect of this invention, a method of cell culture has been developed which demonstrates the resorption, in culture, of both living bone tissue and synthetic bone. One advantage of this process is that the process employs adult-derived cells rather than embryonic or foetal cells used in other techniques. Although it is understood that foetal cells could be used as desired.

As the disease processes of interest are associated primarily with adults, and as it is generally adults who receive bone implants and become space travellers, this culture technique offers a more realistic in vitro testing approach than other methods.

This work has allowed us to examine the morphology of the resorption lacunae created by the osteoclasts and compare these to similar lacunae produced in biological hard tissue substrata (Jones et al, Anat. Embryol 170, 247, 1984).

DETAILED DESCRIPTION OF THE PREFERRED EMBODIMENTS

The thin film as provided on a suitable support, in accordance with this invention, significantly advances the study and understanding of bone cell functional properties. The make-up of the film, as provided in accordance with this invention, permits the culture of bone cells thereon where the surface make-up may be adjusted to encourage a significant degree of resorption of the calcium phosphate entities of the film material through to a negligible degree of resorption of the calcium phosphate entities. The ability to now provide the material in a film which is sufficiently thin that resorption of the entities can be detected by the disappearance of resorbed calcium phosphate entities provides a simple inexpensive format for analysis compared to the prior art techniques. It is particularly surprising that the film make-up, in accordance with this invention, supports the culture of bone cells because of the failures experienced in the past in attempting to culture bone cells and, in particular, osteoblast and/or osteoclast on calcium hydroxyapatite films. The benefit of the invention in providing the film on a transparent supporting substrate, such as quartz or glass, lends to the easy evaluation techniques of the diagnostic process.

Ideally the film thickness is greater than 0.1 microns because it has been found that at film thicknesses less than 0.1 microns it is difficult to obtain uniform homogeneous film coverage, free from discrete voids. As to the upper thickness limit for the film, it can be of any desired thickness depending upon its end use. As will be discussed, the degree of resorption may be detected by light transmittance, which preferably requires a film less than 10 microns in thickness. It is appreciated that thicknesses greater than 10 microns may be useful and those thicknesses may be built up by several repeated applications to the support substrate of the sol-gel made by this invention, where between each application the sol-gel coating is permitted to dry. Preferably the substrate is of quartz or some other thermally tolerant material because of the required sintering of the film once applied to the substrate. Other materials include metals, polymers or ceramic materials other than the film material. Glass may be used when the film material is sintered by use of a surface sintering device which heats the glass surface to a very high temperature for a brief period of time to achieve the degree of sintering necessary in providing the desired type of film. Quartz readily withstands these temperatures and has the desired degree of transparency to permit the conduction of light transmittance tests to determine the extent of resorption of calcium phosphate entities from the film material.

It is appreciated that various aspects of the invention may be implemented in a variety of ways to achieve benefits in the assessment of osteoclast activity. It is appreciated that there are various process implementations for carrying out activity assessment on the film substrata of this invention where the critical factors to be considered in developing the thin film substrata and its impact on bioactivity (ie: bone cell functional properties) include:

i) film uniformity,
ii) film thickness,
iii) film surface morphology (freedom of surface cracks and voids),
iv) film composition,
v) film crystal structure,
vi) film grain size,
vii) percentage of amorphous phase, and
viii) film adhesion to the supporting substrate.

These factors are affected by the following process parameters:

1. Controlled extended aging during a sol-gel process for making the film.
   Correct gelation ensures films can be prepared without voids between deposited particles.
2. Control of process environmental temperature.
   Temperature is preferably maintained at 23°±2° C. to stabilize reaction times and sol viscosity.
3. The pH of the reaction medium is preferably maintained between 11.5 and 12.
4. Cleanliness of the substrate prior to coating application is an important consideration.
5. Control of the dip coating speed also has an impact on film character.
   Substrate removal speed is preferably maintained at 10–20 cm per minute.
6. Temperature and atmosphere of sintering are important considerations.
7. Amounts of reagents for preparing the sols.
8. Rate of combination of reagents.
9. Duration and rate of mixing, including no mixing.
10. Alternatively, duration and conditions of aging, including no aging.
11. Rates and methods of precipitate separation.
12. Process environmental conditions in addition to the above-noted temperature.

The invention as a device may be embodied in the form of a "kit" comprising glass substrates, (or other suitable transparent support) pre-coated with an adherent calcium phosphate thin film, which may be used in a cell culture vessel (possibly a 24-well optionally sterilized multiwell plate i.e. of approximately 15 mm diameter) as a substrata suitable for the culture of mixed bone cell populations. The device is simple and relies on only routine laboratory equipment and techniques for use, is suitable for quantitative analysis, and is inexpensive to fabricate but strong enough to withstand normal levels of handling and may be packaged in lots, of (for example) 24 samples in a plastic presentation box. The thin film surfaces have a defined and reproducible chemistry and are mechanically strong enough to withstand transport when used with an appropriate packing material.

Modifications of the device could be designed for specific applications. For example, each substrate could be presented in a plastic support ring. The latter could be employed not only as a packaging spacer, and thus be sterilized with the substrate, but also a lip to prevent spread of culture medium from the substrate itself and thus facilitate quantification of the resorptive activity. Such protection rings could also be used as stacking devices to enable multiple substrates to be employed simultaneously in the same culture well. The latter could then be enclosed in a sealed culture vessel supplied with circulating medium and could also be adopted for low and zero gravitational environments.

In each case the culture conditions may be such that osteoclasts, in either mononuclear or multinucleate form could be expected to survive in a functional state and resorb the artificial calcium phosphate of the film.

These substrates may be used to assess the resorptive activity of osteoclasts and monitor the change in this level of resorptive activity either as a result of a disease process or the inclusion, in the culture medium, of an agent such as a drug which would influence, either directly or indirectly, osteoclastic resorptive activity.

The device may be used as a means of quantifying the resorptive activity of osteoclasts. Such activity analysis may occur under continuous real-time monitoring, time-lapse intervals or end-point determination. The steps in establishing osteoclast activity are common to each of the above monitoring schedules in that bone cells (either animal or human) are cultured, in specific conditions, on groups of the devices. The culture period is from several hours to many days and preferably from approximately 2 to 10 days (the optimum time is cell species and protocol dependent), during which time the extent of osteoclast activity may be continuously monitored, periodically monitored, or simply not monitored on an on-going basis in favour of final-end-point determination.

Several different osteoclast activity analysis techniques may be employed independently or in combination. The premise of each technique is the quantification of the degree of resorption of the calcium phosphate thin film surface by the osteoclast cells in culture. In detecting the resorption occurrence and in view of the variety of techniques for doing so, it is understood that, by virtue of the thin film nature of this invention, a detection can now be made of the physical disappearance of the calcium phosphate entities. The physical disappearance can now be detected either directly or indirectly.

An example of an end-point optical assessment of the resulting surface involves the removal of each disc from culture such that all cells are removed from the surface, whereupon a routine histological fixative is employed and the device is stained to demonstrate the presence of calcium phosphate. The stain is taken up only in those areas which had not been denuded of the calcium phosphate thin film which would then appear darker than resorbed areas. By placing the device on a standard transmission light microscope it is possible to visualize calcium phosphate denuded areas as light would be transmitted through them. Devices to quantify the amount of light transmitted may be used where the degree of resorption can be quantified, correlating a change in light transmissivity and osteoclast activity. In an extension of this technique, a mirrored surface is applied to the substrate during fabrication of the device and the amount of light reflected from subsequent areas of resorption is quantified using similar imaging techniques. Furthermore, under those circumstances where the composition or structure of the described osteoclast assessment kit does not allow the practical use of standard microscopy instruments, appropriate transmission of the resulting image from the substrate location to remote image analysis equipment could occur via optical fibres or electrical impulse from light detector arrays mounted in proximity to the substrate.

It is also appreciated that other techniques are available to sense the extent of calcium resorption such as by detecting changes in electrical conductivity or capacitance through the film. The electrical properties may be related to the extent of calcium phosphate resorption. The electrical properties may be established by the use of electrically conductive plates or electrodes having the substrate provided therebetween. The extent of the holes as developed by resorption of the substrate would result in changes in the electrical properties of the film located between the plates or electrodes. It is also appreciated that these various techniques may be used individually or one or more of them in combination.

It is recognized that the above techniques may be automated to increase the efficiency of the analysis procedure. The extent of automation may extend from the culture techniques to the analysis of osteoclast activity. In addition, such automation may be configured to link with a computerized database for statistical analysis of resulting data. Furthermore, it is recognized that multiple devices may be evaluated in unison such that an entire 24 well kit (for example) may be assessed at any given time.

In accordance with this invention, for the purposes of reduced gravity investigations on spacecraft (for example), the described analysis techniques and systems would be enclosed in an appropriate transport container. In particular, the remote sensing of osteoclast activity via optical fibres or electrical impulse would assist in the overall packaging of the system to occupy minimal physical space. Within the transport container, the discs may be stacked in groups of 10 (for example) and enclosed in custom built culture vessels. These vessels may be developed as part of a space pre-mission preparation. An example of the culture media handling system present within the culture vessel involves culture fluid being pulsed into the chamber containing the culture plates, from an attached culture fluid reservoir, while the spent medium is evacuated into an attached sump. Each plate may be seeded with cells before final packaging and thus a completely functioning, and self contained unit is presented for pressurized spacecraft payload. The number of culture units per payload may be varied and the complexity of the variables examined would depend on payload space available. The duration of the experiment may be limited to the return flights of the spacecraft and thus no housing on a space station itself is required. The power consumption is controlled within the unit which contains its own power supply and thus not require spacecraft power. Only modest crew time may be required over and above loading and unloading the payload at the start and end of each mission. Data on osteoclast activity could be obtained through both in-flight continuous or lapse time monitoring and post flight end point determination. Data management may be contained within the culture units and data retrieval, in terms of unit performance, may be examined on return. Data analysis directed at the quantification of resorptive activity of the cells may be carried out at a designated laboratory following each mission. It is also appreciated that the system may be used as a diagnostic kit to assess the degree of bone demineralization occurring in particular space crew individuals as a result of long-term exposure to zero gravity conditions.

It is appreciated that the systems and techniques described may be used in various land-based laboratories that create conditions that stimulate either increased gravity, reduced gravity or zero gravity.

Although the provision of pure or essentially pure calcium hydroxyapatite was understood to be the calcium phosphate entity of choice in making the film, we have determined that films which are predominantly of calcium hydroxyapatite do not encourage normal growth developments and, in actual fact, in the presence of osteoclasts very little resorption of the film material is observed. It has been found, however, that by providing a mixture of calcium phosphate entities which include calcium hydroxyapatite and tricalcium phosphate, the degree of resorption is encouraged through a broad range where the film predominantly of tricalcium phosphate provides the highest degree of resorption, whereas a film predominantly of calcium hydroxyapatite provides a negligible degree of resorption. It is this realization, in accordance with this invention, that explains the failure of other calcium phosphate films to encourage normal functional properties in bone cells being cultured on the films. This aspect, in combination with the other aspect of the invention in providing a thin film which permits, for example, transmittance of light, allows one to carry out diagnostic procedures to evaluate several functional properties of bone cells being cultured on the films in accordance with this invention.

Various processing parameters, in accordance with this invention, have been developed to provide on a reproducible basis a range in ratios of calcium hydroxyapatite to tricalcium phosphate for the film make-up. Preferably the ratios range from 10:90 to 90:10, where the lower ratio of 10:90 provides the greatest degree of resorption of the calcium phosphate entities by normally healthy osteoclast-type bone cells and where the upper ratio of 90:10 provides a negligible degree of resorption of the calcium phosphate entities by normally healthy osteoclast-type bone cells. The distinction in respect of identifying normally healthy osteoclasts is that it is understood that various ratios for the film make-up may be used to evaluate abnormal bone cells and, in particular, abnormal osteoclasts to determine their functional characteristics in either a highly resorptive environment or negligible resorptive environment; i.e., at the various ends of the spectrums of the suggested ratios. Furthermore, the various ratios in respect of the mixture of the calcium hydroxyapatite and tricalcium phosphate may be useful in evaluating not only the functional aspects of osteoblasts and osteoclasts, but as well red and white blood cells, stem cells and other cells common to bone. Furthermore, it is understood that the tricalcium phosphate may occur either as α-tricalcium phosphate or β-tricalcium phosphate. The alpha form is preferred for the tricalcium phosphate because of the apparent resorption of the alpha form, although it is understood that the beta form or a combination of alpha and beta forms may be useful from the standpoint of observing resorptive properties of the bone cells.

The calcium phosphate as applied to the substrate is carried out in a manner and in accord with particular chemistry to provide a thin layer predominantly of calcium hydroxyapatite as the preferred form of calcium phosphate on the substrate when minimal or negligible resorption is to be observed.

Calcium hydroxyapatite is a type of calcium phosphate and is present in the inorganic mineral phase of natural vertebrate hard tissue which comprises 60 to 70% of bone and 98% of dental enamel. Its structure has been studied in some detail (J. E. Harris et al., Analysis of the Exafs Spectrum of Hydroxyapatite, J. Phys. C: Solid State Phys., Vol. 19, 6859–6872, 1986; M. D. Grynpas et al., X-Ray Diffraction Radial Distribution Function Studies on Bone Mineral and Synthetic Calcium Phosphates, J. Mater, Sci., Vol. 19, 723–736, 1984) and it has been reported to possess a hexagonal structure with a $P6_3/m$ space group and unit cell dimensions a=b=9.432 Å, c=6.881 Å, where $P6_3/m$ refers to a space group with a sixfold symmetry axis with a threefold helix. In the 1970's, another structure, a monoclinic pseudohexagonal form, space group $P2_1/b$, a=9.421 Å, b=2a, c=6.881 Å, v=120°, was reported (J. C. Elliott, Monoclinic Hydroxyapatite, Science, Vol. 180, 1055–1057, 1973, J. C. Elliott, Monoclinic Space Group Hydroxyapatite, Nature Physical Science, Vol. 230, 72, 1971). The phase transition has been studied (N. Hitmi et. al., OH⁻ Dipole Reorientability in Hydroxyapatites: Effect of Tunnel Size, J. Phys. Chem. Solids, Vol. 47, No. 6, 533–546, 1986; N. Hitmi et al., OH⁻ Reorientability in Hydroxyapatites: Effect of F⁻ and Cl⁻, J. Phys. Chem. Solids, Vol. 49, No. 5, 541,550, 1988).

At room temperature, there are only two kinds of calcium phosphate compounds that are stable when in contact with aqueous solution. The pH of the solution determines which one is the most stable. At a pH lower than 4.2, the compound $CaHPO_4.2H_2O$ (calcium hydrogen phosphate) is the most stable, while at a pH higher than 4.2, hydroxyapatite ($Ca_5$ (OH) $(PO_4)_3$) is the stable phase. At higher temperatures, many other phases can be formed.

Many methods of forming calcium hydroxyapatite powder have been published (S. R. Levitt et al., Forming Method of Apatite Prostheses, J. Biomed. Mater. Res., Vol. 3, 683–685, 1969; H. Homma et al., Preparation of Hydroxyapatite by the Hydrolysis of Brushite, J. Mater. Sci., Vol. 22, 4247–4250, 1987; G. Dewith, Preparation, Microstructure and Mechanical Properties of Dense Polycrystalline Hydroxyapatite, J. Mater. Sci., Vol. 16, 1592–1598, 1981; M. Jarcho et al., Hydroxyapatite Synthesis and Characterization in Dense Polycrystalline Form, J. Mater. Sci. Vol. 11, 2027–2036, (1976); J. Arends et al., A Calcium Hydroxyapatite Precipitated From an Aqueous Solution, Journal of Crystal Growth, Vol. 84, 515–532, 1987).

The following reaction is a preferred embodiment for making calcium hydroxyapatite of this invention.

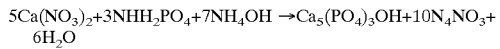

Since hydroxyapatite is stable in neutral and alkaline media, the reaction medium is brought to a high pH value (approximately~12) and the phosphate solution is added drop by drop into the calcium solution to prevent the formation of tetracalcium monohydrogen triphosphate ($Ca_4H(PO_4)_3.2H_2O$) and to obtain a homogenous product. A nitrate solution was employed in this work instead of a chloride, since the nitrate is easy to volatilize during firing.

In the process of making calcium hydroxyapatite films, it has always been thought, in accordance with the prior art, that any impurities were undesirable. It was understood that in the process of plasma spraying hydroxyapatite materials, impurities would be formed which might include α-tricalcium phosphate. However, such impurities were not desired because it appeared that the film, particularly as applied to implants, encouraged a degradation of the character and strength of the film. It is therefore surprising to discover that the presence of tricalcium phosphate and, in particular, the α-tricalcium phosphate, plays an important role in observing functional characteristics of bone cells being cultured on films having a mixture of the tricalcium phosphate with the calcium hydroxyapatite. The tricalcium phosphate is prepared using the same reactants as used in preparing the calcium hydroxyapatite where instead of the preparation of the calcium hydroxyapatite, tricalcium phosphate is prepared. The following reaction scheme is proposed for the preparation of α-tricalcium phosphate.

As it will become apparent in the subsequent discussion involving the formation of the sol-gel containing various ratios of hydroxyapatite to tricalcium phosphate, the amount of tricalcium phosphate produced depends upon a number of process parameters; generally, they include the ratio of reagents used in making the desired calcium phosphate entity, the rate of reaction and aging of the sol-gel and the environment in which the sintering of the film occurs.

The sol-gel process has many advantages (G. Yi et al., Sol-Gel Processing of Complex Oxide Films, Bulletin of the American Ceramic Society, Vol. 70, 1173–1179, 1991) and applications in many fields (G. Yi, et al., Preparation of Pb (Zr,Ti)$O_3$ Thin Films by Sol-Gel Processing: Electrical, Optical and Electro-Optic Properties, J. Appl. Phys. 64(5), 2717–2724, 1988; G. Yi, et al., Ultrasonic Experiments with Lead Zirconate Titanate Thin Films Fabricated by Sol-Gel Processing, Electronic Letters, 25(5), 307–308, 1989; A. A. Hussain et al., Fabrication, Characterization ad Theoretical Analysis of High-T. Y-Ba-Cu-O Superconducting Films Prepared by a Chemical Sol Gel Method, J. Appl. Phys., 70(3), 1580–1590, 1991; M. Sayer et al., Ceramic Thin Films: Fabrication and Applications, Science, Vol. 247, 1056–1060, 1990. In general, there are two kinds of sol-gel technology. The first is "colloidal" method which involves the dispersion of colloidal particles in a liquid to form a sol and then the destabilization of the sol to produce a gel (I. A. M. Askay et al., Colloidal Processing of Ceramics with Ultrafine Particles, pp. 393 in Ultrastructure Processing of Advanced Ceramics, Edited by J. D. McKenzie and D. R. Ulrich, Willey, New York, 1988). The second method uses organometallic compounds as raw ingredients. In aqueous or organic solvents these compounds can be hydrolysed and condensed to form a gel with a continuous network. The gel can be converted into a single phase three dimensional oxide network by sintering or firing at a suitable temperature (Sol-Gel Technology for Thin Films, Fibres, Preforms, Electronics, and Specialty Shapes, Edited by Lisa C. Klein, Noyes Publications, Park Ridge, N.J., U.S.A., 1986). The "colloidal" method is preferred for forming calcium phosphate solution for this substrate coating.

Various techniques may be used to apply the sol-gel to the substrate, For example, the dip-coating method (C. J. Brinker et al., Fundamentals of Sol-Gel Dip Coating, Thin Solid Films, Vol. 201, No. 1, 97–108, 1991) consists of a series of processes: withdrawal of the substrate from a sol or solution at a constant speed, drying the coated liquid film at a suitable temperature, and firing the gel film to a final ceramic.

In spin-coating the solution is dropped on a plate which is rotating at a speed sufficient to distribute the solution uniformly by centrifugal action. Subsequent treatments are the same as those of dip coating.

It is appreciated that there are a variety of other techniques which may be used to apply a thin film of the sol-gel to the substrate. Other techniques include a spraying of the sol-gel, roller application of the sol-gel, spreading of the sol-gel and painting of the sol-gel.

An alternative to coating discrete discs of a singular size is to coat an enlarged substrate with a film of the sol-gel. The entire film on the substrate is then sintered. A device, such as a grid, may then be applied over the film to divide it into a plurality of discrete test zones.

In these various techniques of the sol-gel application, the thickness and quality (porosity, microstructure, crystalline state and uniformity) of formed films are affected by many factors. These include the physical properties, composition and concentration of the starting sol, the cleanliness of the substrate surface, withdrawal speed of the substrate and the firing temperature. In general the thickness depends mainly on the withdrawal rate and sol viscosity for a dip coating process. Therefore, control of the viscosity is very important for controlling the film thickness. Since heterogeneity in the sol is responsible for the formation of macropores and cracks, the coating operation should be undertaken in a clean room to avoid contamination of the sol. At the heat-treatment stage, high temperatures are required to develop the required microstructure.

The purpose of applying the dip coating method to fabricate calcium phosphate films is threefold: (a) to make films with required qualities (uniformity, thickness, porosity, etc.); (b) to make translucent calcium hydroxyapatite films on transparent substrates for biological experiments; and (c) to make multilayer coatings.

X-Ray diffraction analysis of the thin films at sintering temperatures of 400° C., 600° C., 800° C. and 1000°C. demonstrated that films sintered at higher temperatures had higher crystallinity than those sintered at lower temperatures. The peak heights occurring in the X-Ray spectra of films were lower than those observed in the spectra of the starting powders which is most likely due to the orientation or texturing effects of the starting powders.

As noted, the process of this invention may have one or more of its parameters altered to adjust the resultant ratio of calcium hydroxyapatite to tricalcium phosphate in the final sintered layer. Generally, the process of this invention comprises combining a sol of ammonium dihydrogen orthophosphate with a sol of calcium nitrate tetrahydrate over an extended period to form a sol-gel. The support substrate is then dipped in the sol-gel and removed therefrom, preferably at a constant velocity to form a film on at least one surface of the sol-gel. The substrate with freshly applied coating is allowed to dry and is then sintered at a high temperature to form a solid film having a mixture of calcium hydroxyapatite to tricalcium phosphate. The ratio of these two entities the film morphology and the resultant bioactivity is each determined by varying conditions in the steps of preparing the sol, applying the substrate and sintering the film. The variable conditions which are used may be:

1. amounts of reagents for preparing the sols.
2. Rate of combination of reagents.
3. Duration and rate of mixing, including no mixing.
4. Alternatively, duration and conditions of aging, including no aging.
5. Rates and methods of precipitate separation.
6. Process environmental conditions in addition to the above-noted temperature.
7. The extent of mixing during and after combination of the sols.
8. Velocity of removal of the substrate from the sol-gel to thereby vary the film thickness for the dip process.
9. The sintering temperature.
10. Sintering of the material in a controlled atmosphere, such as an inert gas, a vacuum or an atmosphere with water vapor present.

By varying the temperature at which the film is sintered, a range in ratios of calcium hydroxyapatite to tricalcium phosphate may be achieved without varying any of the other parameters of the process. It has been found that in sintering a film at temperatures ranging from approximately 800° C. to approximately 1100° C., the film composition may vary from predominantly calcium hydroxyapatite through to predominantly tricalcium phosphate which, according to diffraction patterns, would indicate that it is α-tricalcium phosphate.

Exemplary procedures are provided for the preparation of the film in accordance with this invention where the range in ratios of calcium hydroxyapatite to tricalcium phosphate can be achieved, and furthermore, where the film may be made predominantly of either calcium hydroxyapatite or tricalcium phosphate.

PROCEDURE 1

The following procedure is based on preparing sufficient sol-gel to coat a limited number of substrate discs. As per the above-noted chemical reaction, solution A comprises a calcium nitrate which is preferably calcium nitrate tetrahydrate. Solution B comprises an ammonium phosphate which is preferably ammonium dihydrogen orthophosphate (mono basic). Solution A is mixed with solution b to produce the desired solgel, sol c. Solution A is prepared by adding 40 mls of doubly distilled water to 4.722 grams of calcium nitrate—$Ca(NO_3)_2$. The solution is stirred at moderate speed for sufficient time to dissolve all of the calcium nitrate which is normally in the range of 3 minutes. To this solution, 3 mls of ammonia hydroxide ($NH_4OH$) is added and stirred for approximately another 3 minutes. The pH of the solution is tested where a pH of about 12 is desired. To this solution is added 37 mls of double distilled water to provide a total solution volume of approximately 80 mls. The solution is stirred for another 7 minutes and covered.

Solution B is prepared by adding 60 mls of double distilled water to a 250 ml beaker containing 1.382 grams of $NH_4H_2PO_4$. The beaker is covered and stirred at moderate speed for 3 to 4 minutes until all $NH_4H_2PO_4$ is dissolved. To this solution is added 71 mls of $NH_4OH$ and the beaker then covered and stirring continued for approximately another 7 minutes. The pH of the solution is tested where a pH of about 12 is desired. To this is added another 61 mls of double distilled water and the beaker covered to provide a total solution volume of approximately 190 mls. The solution is then stirred for a further 7 minutes and covered.

The desired sol gel is then prepared by combining solution B with solution A. All of solution A is introduced to a 500 ml reagent bottle. Stirring is commenced at a moderate speed and solution B introduced to the reagent bottle at a rate of approximately 256 mls per hour until all of solution B is delivered into solution A. After completion of this addition and combination of solution A with solution B, the resultant solution is continued to be stirred at moderate speed for approximately 22 hours. The resultant sol-gel is inspected for any abnormal precipitation or agglomeration. If any abnormal precipitation or agglomeration has occurred, the solution must be discarded and preparation commenced again. The sol is then carefully transferred to another 500 ml reagent bottle so as to avoid any inclusion of particle agglomerations that may be present on the walls of the original reagent bottle. Approximately 240 mls of sol C, that is the resultant sol, is delivered to a centrifuge bottle and centrifuged for 20 minutes at about 500 rpm at room temperature. Following centrifugation, 180 mls of supernatant is discarded without disturbing the sediments. The sediments are gently resuspended by mixing in a smooth rotating manner for about 30 minutes. Viscosity of the sol is then measured and preferably is between 20 to 60 cP. The sol is then ready for dip coating of the selected substrate.

PROCEDURE 2

Cleaning of quartz disc as a preferred substrate—the discs are placed in a glass beaker and chromic acid cleaning solution is supplied to the glass beaker to cover all discs. The beaker is then covered. The discs are then sonicated in a water bath for 1 hour. The acid is washed away using tap water for 20 minutes. The residual tap water is removed by three changes of doubly distilled water. After the final change of double distilled water, every single disc is dried with lint-free towel and inspected for flaws in the quartz surface. Any residual particulate on the surface is as needed with compressed nitrogen or air. The discs are stored in covered trays in an aseptic environment, although it is understood that under certain culture conditions, discs that have been sterilized are not required.

PROCEDURE 3

The quartz disc substrate as a preferred substrate is dipped in the sol prepared by Procedure 1. The disc is grasped at the edges to avoid touching the surface. The disc is dipped in the sol, preferably by machine. The disc is removed from the sol at a prescribed withdrawing velocity. The coating on one side of the dish is removed. The coated substrate is then placed in a clean petri dish and covered and dried at room temperature. This procedure is repeated to build up as necessary the desired coating thickness. The film, as formed prior to sintering, should be uniform without cracks, clumps or voids.

PROCEDURE 4

Sintering of the calcium phosphate film—the discs in a suitable holder are placed in a furnace. The furnace is elevated to a temperature of 1000° C., or whatever other desired sintering temperature and the discs sintered at that temperature for approximately 1 hour. The substrates as sintered are allowed to cool within the furnace and are removed and loaded into plastic packaging trays.

The composition of the films may be analyzed by any suitable procedure, such as x-ray diffraction, to evaluate based on the diffraction patterns the relative amounts of calcium hydroxyapatite and tricalcium phosphate usually in the form of $\alpha$-tricalcium phosphate.

By following Procedure 1 and sintering at four different temperatures; namely 800° C., 900° C., 1000° C. and 1100° C., a variety of calcium phosphate entity mixtures are achieved. At 800° C., the film is predominantly calcium hydroxyapatite; whereas sintering at 900° C. provides approximately 70% calcium hydroxyapatite and 30% tricalcium phosphate. At 1000° C., the film has a majority of tricalcium phosphate and a ratio of approximately 10:90 of calcium hydroxyapatite to tricalcium phosphate. Sintering at 1100° C. provides a film which is predominantly tricalcium phosphate.

However, when the film is applied as per Procedure 1 and then is sintered in a vacuum at 1000° C., the ratio is approximately 66:34.

The capability of offering thin films of different composition is important because:

1. the selection of film composition allows different standards of activity to be assessed for both normal and abnormal cell populations. Specifically, abnormal behaviour may become apparent in a test employing a relatively slow resorbing material versus a relatively fast test and vice versa.
2. The selection of film composition may be based on a desire to investigate the performance of bone cells, both normal and abnormal, on a film that is similar to materials implanted in the body. This is a potential application for a predominantly HA film, as implants are commonly supplied with a coating that is predominantly HA.
3. The selection of film composition can influence the activity of cells other than osteoclasts thereby offering additional information on the performance of the cell population under examination.

Typically, a cell culture protocol defines a fixed period of exposure of the film to cellular activity. At any time during the cell culture period, assessment of cellular activity is both difficult and potentially misleading as the cells present can reside on top of the area where resorption has taken place. Consequently, any comprehensive evaluation of the surface requires the removal of all cellular material so that the surface can be freely assessed. This necessitates a standardized exposure protocol.

Since the exposure time is then fixed in a given comparative study, the degree of resorption occurring on the device of this invention can be expressed as the percentage of the film removed by the osteoclasts versus the total film exposed to the media. As the film is thin and of uniform thickness, the amount of material removed can be related to the plan area of the created voids. This accurate two-dimensional assessment of a three-dimensional resorption event greatly simplifies the techniques required to assess the degree of resorption, versus that necessary to evaluate conventional bone slices that exhibit complex irregular three-dimensional resorption pits of no fixed depth. In the use of the device of this invention, a high degree of resorption is expressed as large often interconnected voids in the film with characteristic organic perimeter outlines (of a scalloped nature). In contrast, a low degree of resorption is expressed as infrequent pinholes in the film creating a punctate topography.

The practical determination of the degree of resorption is possible through the use of a variety of techniques. Examples of optical methods are:

1. the films can be examined by light microscopy and the total area of resorption visually estimated. For improved viewing contrast, the films may be stained or not at the operator's discretion with a calcium specific stain.
2. The films can be placed in different beams of monochromatic light of selected wavelengths and the level of light absorption for different wavelengths determined electronically and subsequently correlated to the degree of resorption.
3. The films can be placed in a software-based image analysis system and the resulting image analyzed on a pixel by pixel basis having defined threshold limits for the detection of resorbed areas.

Based on the various bone cell cultures that we have completed, the minimum detectable level of resorption is considered to be the presence of a single resorption void of diameter 100 µm. As the area of film coverage on the samples evaluated was approximately 100 sq.mm, this resorption void represents a percentage resorption of approximately 0.01%. Examples of predominantly HA films have typically exhibited this low level of resorption. In contrast, the highest level of resorption observed has been present on predominantly TCP films where resorption in the range of 20% to 50% is common. There is always a degree of variability in the biological test as uniform osteoclast seeding densities on the surface of the disc cannot be strictly attained. What is clear is that the degree of resorption occurring on a predominantly HA film versus a predominantly TCP film will differ by approximately two orders of magnitude for equivalent cell seeding densities.

Although, as noted, there are a variety of procedures in which the substrate of this invention, as coated with a thin film of calcium phosphate entities may be used in assessing osteoclast activity, a suggested technique is exemplified as follows:

Within the confines of a laminar flow hood, sol-gel coated 12.7 mm diameter quartz discs are placed in the 24 wells of a non-culture treated 24 well tray. This culture unit is closed with a lid, and inserted into a sterilizing bag which is then sealed.

Sterilization is achieved using gamma irradiation of 2.5 MegaRads.

Cells are obtained from the femoral bone of young adult male Wistar rats (approximately 120 gm) using a modified method originally developed by Maniatopoulos et al. in 1988. Working in a laminar flow hood following excision, both femora are passed through four 10 ml washes of α-Minimal Essential Medium (α-MEM) containing 1.0 mg/ml penicillin G, 0.5 mg/ml gentamicin, and 3.0 ug/ml fungizone. The epiphyses are then cut off and the flushed out from each femur using 10 ml per femur of α-MEM supplemented with 15% foetal bovine serum, 50 ug/ml ascorbic acid (added as 1 % of a 5 mg/ml freshly thawed stock solution in phosphate buffered saline), 10 mM Na b-glycerophosphate (added as 1 % of a 1M stock solution in double-distilled water), and antibiotics at 1/10th of the concentration described above.

The resultant 20 ml of bone cell suspension is combined and by being pipetted up and down gently using a 25 ml pipette.

Each disc within its well is inoculated with 1 ml of this explant cell suspension.

The following day the culture medium containing unattached cells is removed by aspiration, and the cultures re-fed with 2 ml per well of freshly prepared identical medium. This process is repeated 3 times a week, for a period of 1–2 weeks.

During the cell culture period, the activity of the osteoclasts present on the discs may be observed and recorded through the use of an environmentally controlled microscope stage with attached video hardware. Selected discs are removed from the culture tray using sterile tweezers, and inserted into a 35 mm diameter lidded culture dish containing 4 ml of $CO_2$ independent α-MEM (Gibco 320-8045AJ) with L-glutamine (Gibco 320-5030PE) in the proportion of 20 ul to 10 ml of culture medium (additionally supplemented as described above).

This dish is then sealed circumferentially using Parafilm to minimize medium evaporation and placed in the Nikon inverted phase microscope videotaping incubation chamber whose temperature has been stabilized at 37° C. A green filter (wave-length 520 to 550 nm) is used with a 20× objective lens for optimal definition.

Videotaping is performed with a Sony time-lapse recorder and an 8 mm videotape (frame speed ranging from 1 frame/8 seconds to 1 frame/4 seconds, depending on cell mobility). A single field may be taped for a period of 1–2 days at a time, or even longer if conditions warrant this.

A photographic record can be obtained, for quantitative or other purposes, from a Sony monitor with a resolution of 950 horizontal lines (model PVM 122).

Following the completion of the cell culture protocol, the extent of resorption present on the discs is observed by removing the discs from the culture tray, eliminating any residual cells or particulate present on the surface of the disc, and viewing the disc under a phase contrast microscope at magnifications of 100× to 400×.

Although preferred embodiments of the invention are described herein in detail, it will be understood by those skilled in the art that variations may be made thereto without departing from the spirit of the invention.

I claim:

1. A culture substrate for culturing bone cells in vitro to permit evaluation of bone cell functional properties comprising:
   a calcium phosphate based thin film provided on a support substrate wherein said thin film comprises calcium phosphate entities which provide for varying degrees of resorption of said calcium phosphate entities in evaluating said functional properties, said film being sufficiently thin that the degree of resorption of said entities can be determined by the detection of a physical disappearance of calcium phosphate entities.

2. The culture substrate of claim 1 wherein said calcium entities include a mixture of calcium hydroxyapatite and tricalcium phosphate, relative amounts of said entities varying said resorption wherein predominantly tricalcium phosphate provides the highest degree of resorption and predominantly calcium hydroxyapatite provides negligible degree of resorption.

3. The culture substrate of claim 2 wherein said entities are in a ratio of calcium hydroxyapatite to tricalcium phosphate selected from the ratio range of 10:90 to 90:10,
   where the lower ratio of 10:90 provides the greatest degree of resorption of said calcium phosphate entities by normally healthy osteoclast type of bone cells, and where the upper ratio of 90:10 provides a negligible degree of resorption of said calcium phosphate entities by normally healthy osteoclast type of bone cells.

4. The culture substrate of claim 3 wherein said ratio is selected from the group of ratios 15:85, 66:34 and 90:10.

5. The culture substrate of claim 1 wherein said film is of a thickness in the range of 0.1 µm to 1 µm.

6. The culture substrate of claim 1 wherein said thin film permits detection of said physical disappearance of said calcium phosphate entities by a technique of detecting a change in light transmittance, light refraction, light reflection, electrical conductivity, electrical capacitance or a combination of one or more of the techniques.

7. The culture substrate of claim 1 wherein said support substrate is transparent and physical disappearance of said calcium phosphate entities is detected by detecting a change in light transmitted through said thin film.

8. The culture substrate of claim 1 wherein said support substrate is of quartz, glass, metal, polymers or ceramic materials other than a calcium phosphate.

9. A device for use in an analytical or diagnostic system for evaluation of bone cell functional properties, said device comprising:

a containment well;

a culture substrate as recited in claim 1, said culture substrate positioned in said well with said film positioned upwardly of said well; and means for covering said well until used.

10. The device of claim 9 wherein said support substrate is of quartz, glass, metal, polymers or ceramic materials other than calcium phosphate.

11. A device for use in an analytical or diagnostic system for evaluation of bone cell functional properties, said device comprising:

a culture substrate as recited in claim 1; and means for dividing said film into a plurality of discrete test zones.

12. A sol-gel process for making a culture substrate having the properties in accordance with claim 1, said sol-gel process comprising:

preparing a sol-gel by combining a solution of ammonium phosphate with a solution of calcium nitrate over an extended period to form a sol-gel;

applying to a support substrate said sol-gel on at least one surface of said support substrate to form said film; and sintering said film coated substrate to form a solid film of a ratio of calcium hydroxyapatite to tricalcium phosphate, said ratio being determined by varying conditions in said steps of preparing a sol-gel, applying said sol-gel to a support substrate and sintering said film.

13. The process of claim 12 wherein said varying conditions being one or more of degree and extent of mixing during and after combination of said ammonium phosphate and calcium nitrate solutions during aging, sintering temperature and sintering in a controlled atmosphere.

14. The process of claim 13 wherein said film is sintered in a vacuum as said controlled atmosphere to favor an intermediate ratio of said entities.

15. The process of claim 13 wherein said film is sintered at a temperature selected from the range of 800° C. to 1100° C., the higher the selected temperatures, the lower the ratio of calcium hydroxyapatite to tricalcium phosphate.

* * * * *

UNITED STATES PATENT AND TRADEMARK OFFICE
CERTIFICATE OF CORRECTION

PATENT NO. : 5,849,569
DATED : December 15, 1998
INVENTOR(S) : Davies

It is certified that error appears in the above-identified patent and that said Letters Patent is hereby corrected as shown below:

Column 16, line 48, begin new sub-paragraph with "where"; line 54, "1µm" should read --10µm--.

Signed and Sealed this

Fourth Day of May, 1999

Attest:

Q. TODD DICKINSON

Attesting Officer

Acting Commissioner of Patents and Trademarks